United States Patent [19]
Zanen et al.

[11] Patent Number: 5,765,552
[45] Date of Patent: *Jun. 16, 1998

[54] INHALER DEVICES PROVIDED WITH A RESERVOIR FOR SEVERAL DOSES OF MEDIUM FOR INHALING, TRANSPORTING DEVICE, WHIRL CHAMBER

[75] Inventors: Pieter Zanen, Houten; Adrianus Plomp, Schoorl; Gerhardus Anthonius Boon, Wormer; Roy van Swieten, Nieuwkuyk, all of Netherlands

[73] Assignees: Pharmachemie B.V.; Raytec B.V., both of Netherlands

[*] Notice: The term of this patent shall not extend beyond the expiration date of Pat. No. 5,429,122.

[21] Appl. No.: 451,810

[22] Filed: May 26, 1995

Related U.S. Application Data

[63] Continuation of Ser. No. 42,245, Apr. 2, 1993, Pat. No. 5,429,122, which is a continuation-in-part of Ser. No. 859,433, filed as PCT/EP91/01884 Sep. 26, 1991, abandoned.

[30] Foreign Application Priority Data

| Sep. 26, 1990 | [NL] | Netherlands | 9002103 |
| Jul. 15, 1991 | [NL] | Netherlands | 9101245 |
| Sep. 20, 1991 | [NL] | Netherlands | 9101593 |

[51] Int. Cl.$^6$ .................. A61M 15/00; A61M 16/00; B05D 7/14; B65D 83/06
[52] U.S. Cl. .................. 128/203.15; 128/203.12; 128/203.23
[58] Field of Search .................. 128/203.12, 203.15, 128/203.21–203.23

[56] References Cited

U.S. PATENT DOCUMENTS

| 1,459,478 | 6/1923 | Page . | |
| 1,858,735 | 5/1932 | Goodsell | 128/203.15 |
| 2,001,207 | 5/1935 | Mcmanamna et al. | 128/203.15 |
| 2,581,182 | 1/1952 | Fields . | |
| 4,036,223 | 7/1977 | Obert | 128/203.15 |
| 4,274,403 | 6/1981 | Struve . | |
| 5,046,493 | 9/1991 | Kropkowski et al. | 128/203.15 |
| 5,176,132 | 1/1993 | Drought et al. | 128/203.21 |
| 5,201,308 | 4/1993 | Newhouse | 128/203.15 |
| 5,429,122 | 7/1995 | Zanen et al. | 128/203.15 |

FOREIGN PATENT DOCUMENTS

| 0211595 | 2/1987 | European Pat. Off. . |
| 2347939 | 11/1977 | France . |
| 2489116 | 3/1982 | France . |
| 2598918 | 11/1987 | France . |
| 4004904 | 9/1990 | Germany . |
| 1118341 | 7/1968 | United Kingdom . |
| 1515265 | 6/1978 | United Kingdom . |
| 2165159 | 4/1986 | United Kingdom . |

*Primary Examiner*—Kimberly L. Asher
*Attorney, Agent, or Firm*—Webb Ziesenheim Bruening Logsdon Orkin & Hanson, P.C.

[57] ABSTRACT

The present invention provides an inhaler device for inhaling an aerosol in a desired dosage, comprising a housing in which is received a reservoir of powder or liquid, an inhaling piece placed on the housing and a mechanism for transporting the powder or liquid from the reservoir to the inhaling piece in a dosage required for the aerosol. A spring biased piston is incorporated into the housing to compress the inhalable medium in the reservoir. The inhalable medium transporting mechanism includes a recess within a reciprocating plunger. The inhaling piece includes two separate air intake openings extending to an exterior of the inhaling piece. The two air intake openings generate separate colliding streams of air which transport and mix the inhalable medium.

11 Claims, 8 Drawing Sheets

INHALER DEVICES PROVIDED WITH A RESERVOIR FOR SEVERAL DOSES OF MEDIUM FOR INHALING, TRANSPORTING DEVICE, WHIRL CHAMBER

RELATED APPLICATION

This is a continuation of U.S. application Ser. No. 08/042,245, filed Apr. 2, 1993, now U.S. Pat. No. 5,429,122, which is a continuation-in-part of U.S. application Ser. No. 07/859,433, filed May 26, 1992, now abandoned, which is a continuation of International Application No. PCT/EP91/01884 filed Sep. 26, 1991, now abandoned.

BACKGROUND OF THE INVENTION

1. Field of the Invention

The present invention relates to inhaler devices, in particular inhaler devices with which several doses can be administered. With such inhaler devices an aerosol is administered as medicine to the lungs, particularly the alveolar zone, by inhalation through nose or mouth.

2. Prior Art

Existing systems typically provide a single dose of an aerosol, whereafter a capsule is thrown away, which is harmful to the environment. Inhaler devices, for instance for CNSLD patients, wherein at each inhalation a capsule is placed therein, are frequently used in practice.

Inhaler devices for several doses are still only commercially available on a limited scale. There are problems with these known inhaler devices in respect of their manageability and size, the required suction force on a mouth or nose piece and/or the accuracy of dosing.

Known inhaler devices for several doses are awkward to use and/or consist of a relatively large number of components, whereby manufacture becomes time-consuming and expensive. Such

DESCRIPTION OF THE PREFERRED EMBODIMENTS

An inhaler device 1 (FIGS. 1–3) according to the present invention comprises a housing 2 in which a reservoir 3 of inhalable material, which is medicinal in the embodiment shown, is held in a compressed stated. Placed on the housing 2 is an inhaling piece 7, for example joined thereto in a manner not shown with a snap-on connection, so that after the reservoir has been emptied the inhaling piece can be placed on a new reservoir. The inhaling piece 7 is intended for placing on nose or mouth in order to be then sucked on. Placed over the inhaling piece 7 is a removable closing cap 8 provided with a protruding pin 9.

Figure 2:
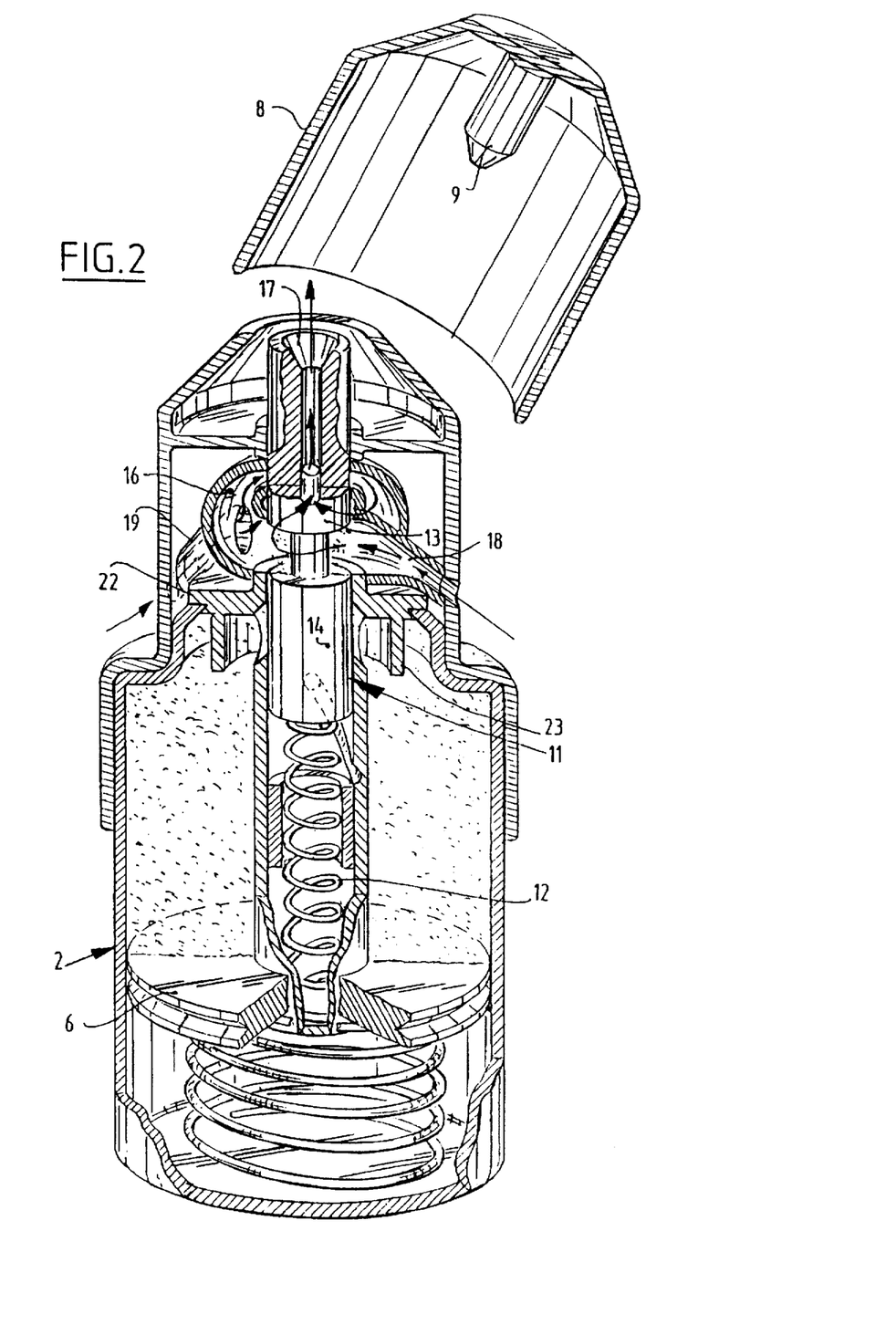

As will be apparent particularly from FIG. 2, when the closing cap 8 is removed, a plunger 11 is moved upward by means of the spring force of a second coil spring 12. The plunger 11 is provided with a recess between a top piece 13 and a bottom piece 14, wherewith a dose of powder can be transported in the desired dosage from the reservoir to a mixing space 16. As is indicated with the arrows, when the opening 17 is sucked on, suction takes place through three channels, of which the channels 18 and 19 are visible in the figure, and via whirling of the air a good mixing of the powder and the air is obtained in the desired manner.

Figure 1:
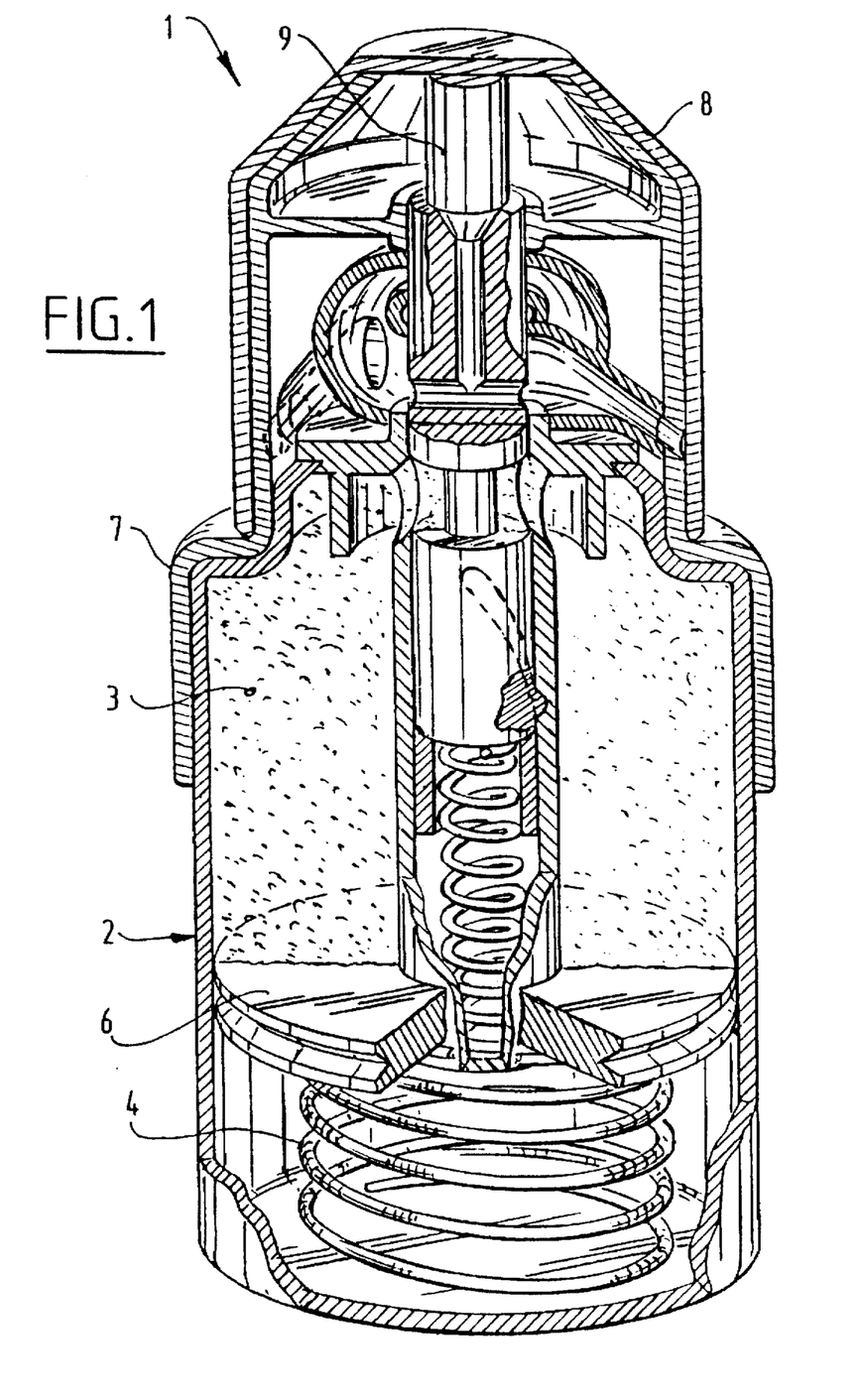

In preference the pin portion 9 of the closing cap 8 is provided with a tapering portion which fits into the conical opening 17 so that when the closing cap 8 is arranged the up and downward movable plunger 11 provided with a central channel 21 and the recess can be moved into the rest position show in FIG. 1.

For guiding the powder to the recess in the plunger the housing 2 is preferably provided with an upper piece 22 provided with collar-like portion 23 which protrudes into the powder reservoir.

So that the powder-form material is carried well by the plunger, the latter is provided with a protrusion guided in a groove 24 that is arranged in the cylinder-shaped guiding 25 for the plunger, wherein this groove 24 causes the plunger to rotate slightly.

Figure 3:
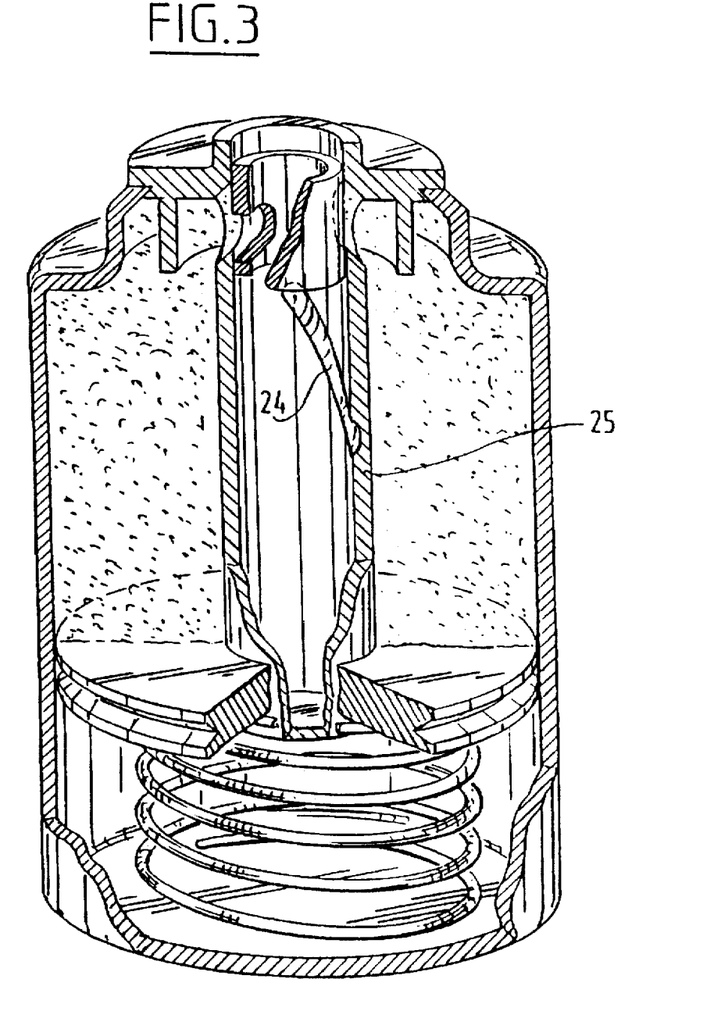
Figure 4:
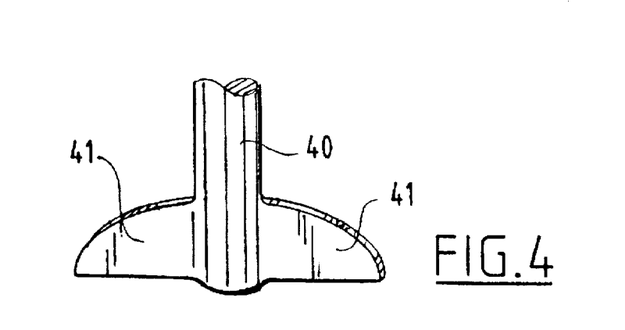
FIG. 4 shows a view of an element to be included in the embodiment of FIGS. 1–3.

In a further embodiment of the present invention (not shown), a shaft 40 provided with wing-like elements 41 can be included at the center line of the device shown in FIGS. 1–3. Preferably a rotating mechanism is provided such that for every dose shaft 40 is rotated and powder is stirred by elements 41 whereby the flow of the powder is improved. The rotating mechanism can correspond to such mechanism as used in a ballpoint pen for rotating the writing element thereof.

The present inhaler device is suitable for giving a large number of doses and therefore for prolonged use. It can be manufactured from a comparatively small number of components, preferably of plastic.

Figure 5:
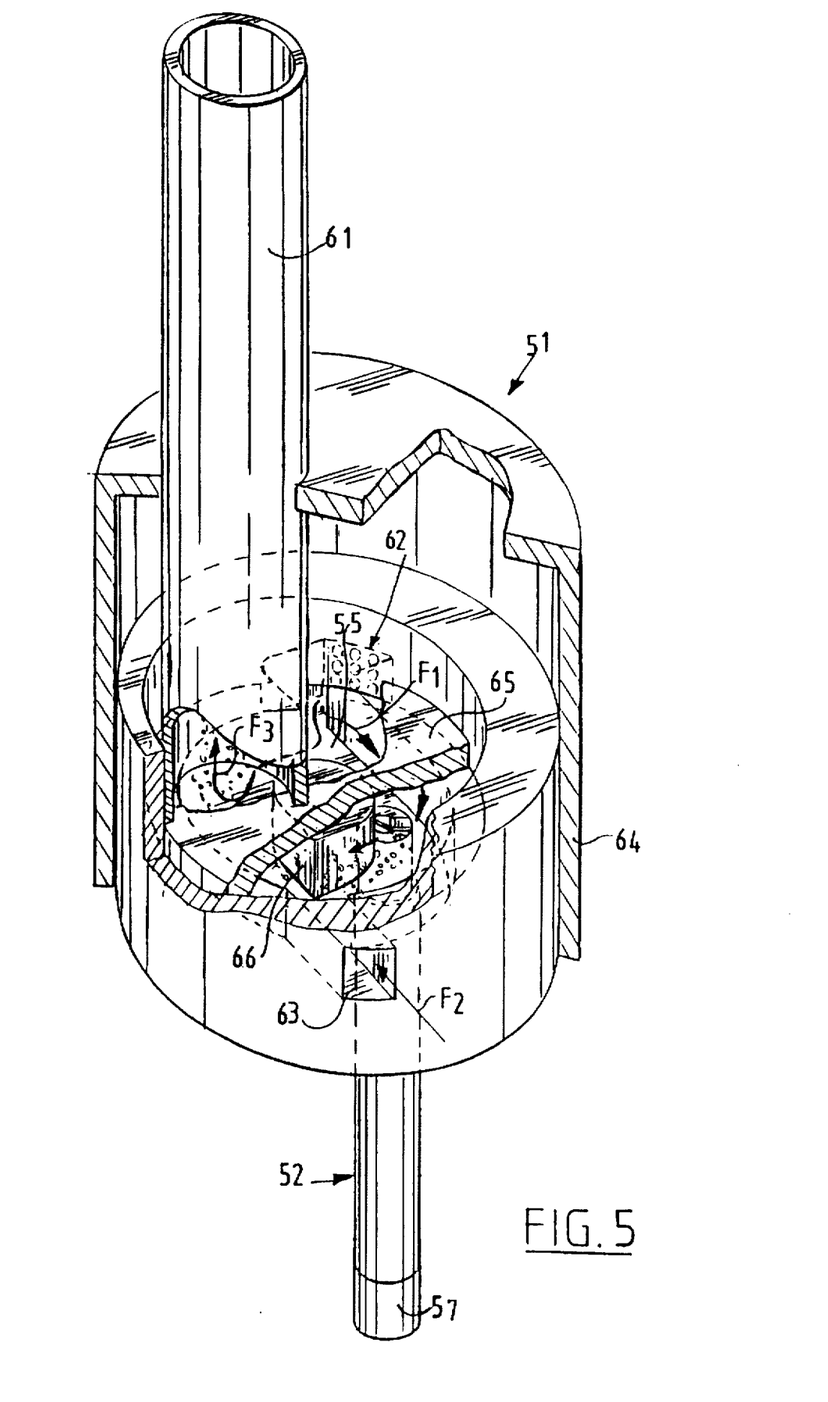
FIG. 5 shows a partly broken away view in perspective of a second preferred embodiment of the inhaler device according to the present invention.
Figure 6:
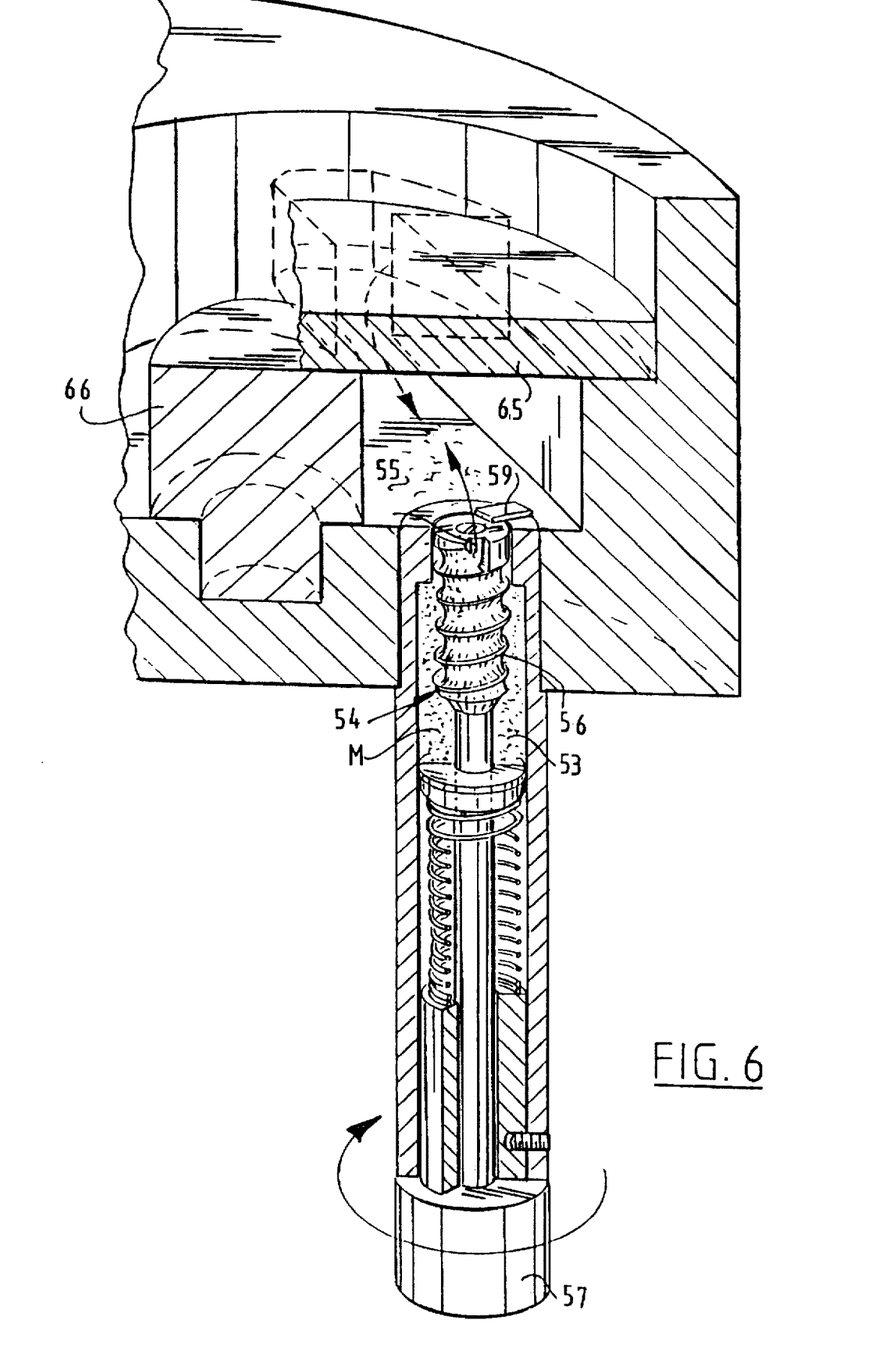
FIG. 6 is a view, partly in perspective and partly in section, of detail II of FIG. 5.
Figure 7A:
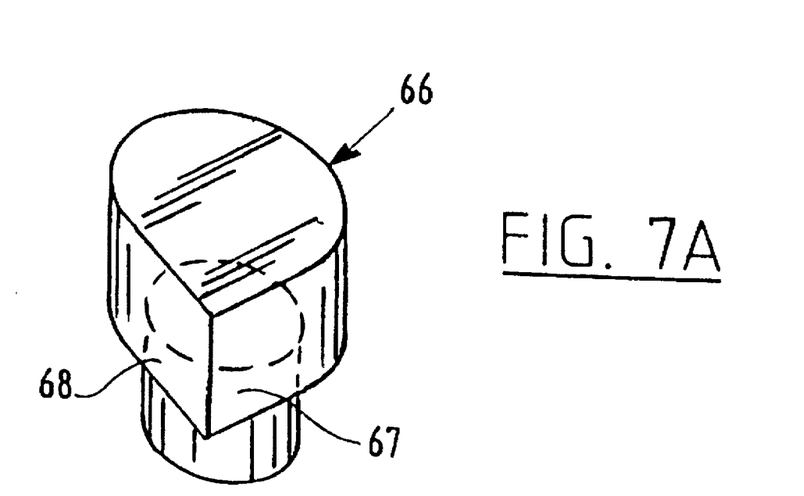
FIG. 7A and FIG. 7B respectively show elements which can be incorporated in the embodiment as shown in FIG. 5 and FIG. 6.
Figure 7B:
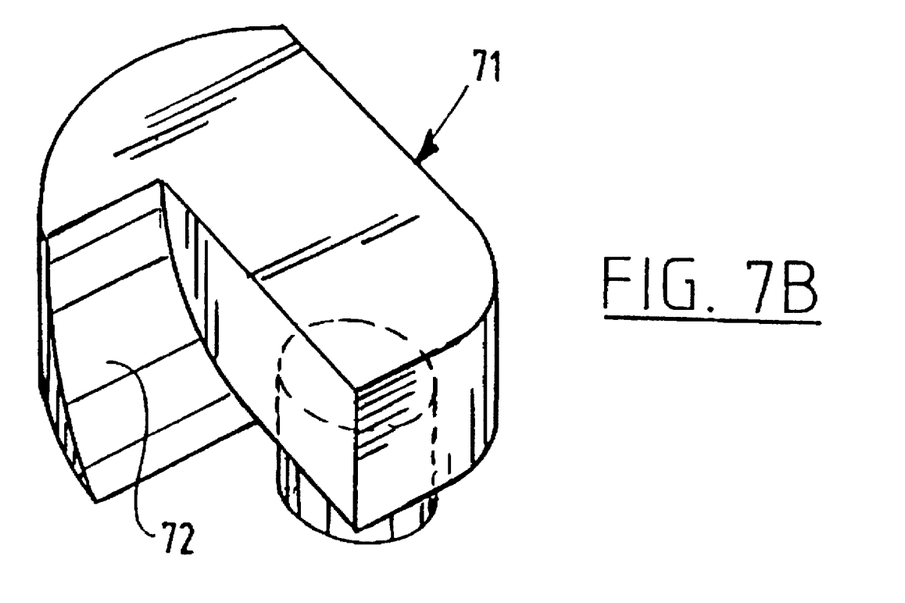

A second embodiment, an inhaler device 51 (FIG. 5), is provided with a part 52 (FIG. 5, FIG. 6) in which is received a reservoir 53 for medium for inhaling in addition to a transporting mechanism 54 for transporting the medium out of the reservoir to a whirl chamber 55. The material for inhaling comprises carrier particles which are of minor importance in the effect on the bronchial tubes of a patient. These carrier particles are necessary however in order to prevent the medium M for inhaling from coagulating and thereby becoming barely transportable.

For transporting the medium M in doses of precise size a screw or worm 56 is preferably used which can be operated using a rotating knob 57. Worm or screw 56 has threads inherent in all worms or screws, and as the threads are in contact with the medium M, the medium is transported along the threads of the screw or worm 56 as knob 57 is turned. The medium M is thus transported out of the reservoir 53 into the whirl chamber 55 through opening 58. It has been found in tests that such a transporting mechanism is capable of transporting a medium M with an accuracy of less than 5% out of the reservoir 53 into the whirl chamber 55 at each revolution of the opening 58 away from and up to a closing member 59 for this opening.

The inhaler device is provided with an inhaling piece 61 for sucking in air via the nose or mouth of a patient along two feed channels 62 and 63 which are arranged in a peripheral wall 64 of the inhaler device. A flow of air, as designated with arrows $F_1$, carries the medium brought into the whirl chamber 55 under cover plate 65 along a guide means 66 and then collides with the air flow designated with arrow $F_2$ which is drawn in along feed channel 63. With a comparatively small suction force great air speeds occur here, in addition to whirls when these air flows $F_1$ and $F_2$ collide with one another. Shear forces hereby occur which separate the particles with medicinal effect from the carrier particles which usually have a greater diameter than that of the medicinal particles.

The member 66 for guiding the air (FIG. 7A) is provided on the side facing the feed channel 62 with a rounded form, while the side facing the feed channel 63 is sharp-edged and the angle is formed by flat wall portions 67 and 68 so that the air flow $F_2$ collides with the air flow $F_1$ transversely.

In a further embodiment (not shown), the inhaler devices according to the present invention is provided with a guide means 71 for guiding the air (FIG. 7B) partially similar to the guide means 66, but which is additionally provided with an air guide portion 72 rising in the direction of the inhaling piece 61 and preventing unwanted air, as indicated with arrow $F_3$ in FIG. 1, on the side of the guide means 71 remote from the doses of medium for inhaling from passing into the inhaling piece 61. An inhaler device provided with such a guide means 71 therefore requires an even smaller suction force, which is particularly important in the case of children and older patients with lung disorders.

The inhaler device according to the shown and described embodiment has, among others, the following advantages:

- the inhaler device is compact of structure and has a size such that it can easily be held in the hand;
- the inhaler device can be used in any desired position, with the inhaling piece horizontal or oriented upward or downward;
- the inhaler device requires little suction force, while great shear forces are applied to the medium or powder so that the medicinal particles are released from the carrier particles.

A third embodiment of an inhaler device 81 (FIG. 8) according to the present invention comprises a schematically designated mixing chamber 82 in which a dosage for inhaling is mixed with air drawn into the mixing chamber 82 in a manner not shown. The inhaler device 81 can further be provided with a reservoir in which is received a supply of medium for inhaling, in addition to transporting means, likewise not shown, for transporting one dose of medium at a time out of this reservoir into the mixing chamber.

Figure 8:
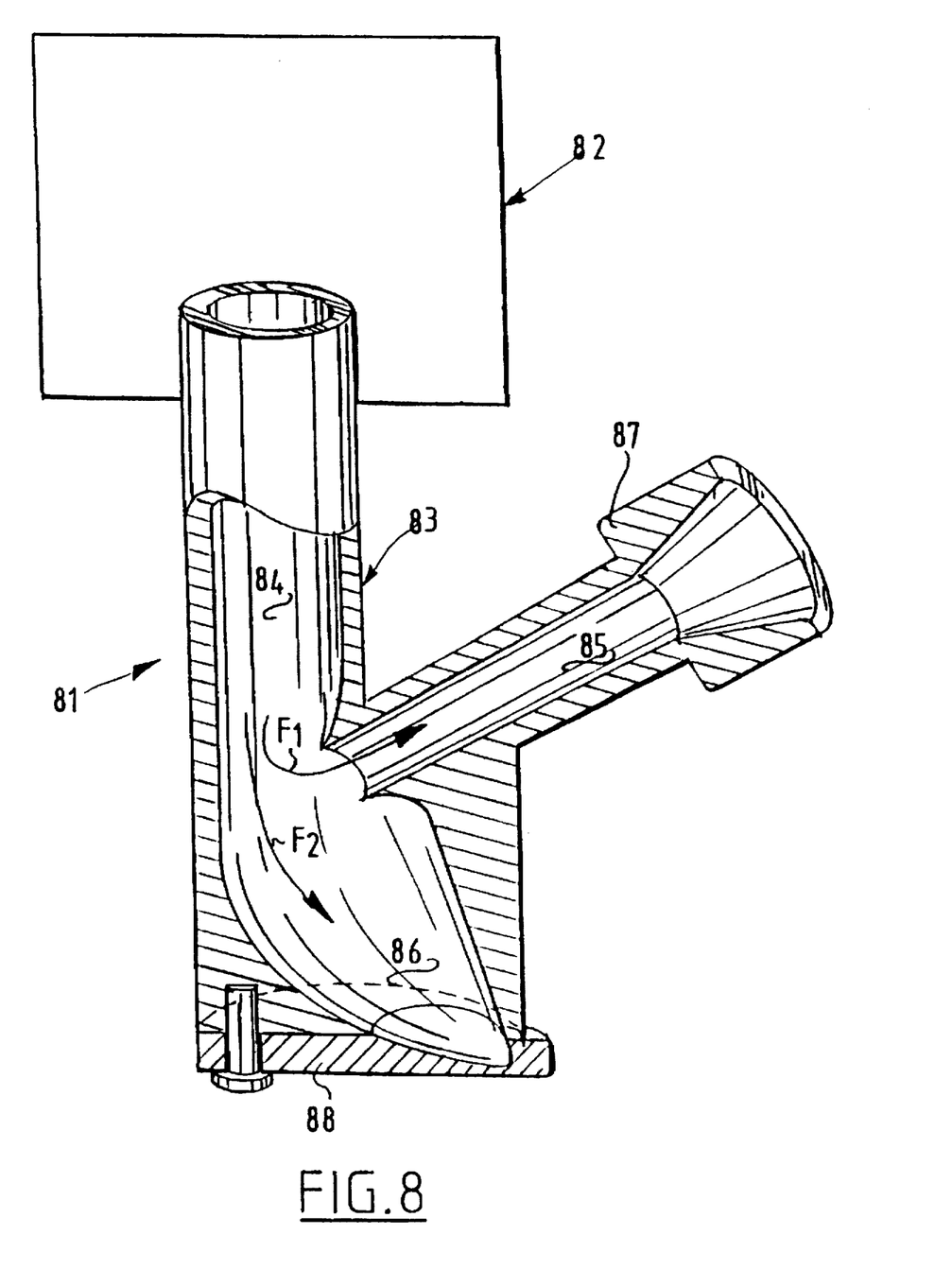
FIG. 8 shows a side view of a third embodiment, partly in section, of the inhaler device according to the present invention.

Coupled to the mixing chamber 82 is a suction piece 83 comprising an inlet channel 84, an outlet channel 85 and a collecting chamber 86. The suction piece 87 is sucked on by the patient via nose or mouth. A fraction of the aerosol, designated with arrow $B_2$ whereof the particles have a comparatively large diameter, for example greater than 10, 7, 5 or 1 µm, does not however reach the outlet channel 85 of the mass of the particles. These particles from the fraction $B_2$ are collected at the bottom of the collecting chamber 86 which must be emptied from time to time by releasing the cover 88.

With the inhaler device (third embodiment) according to the present invention now proposed and still to be realized in practice, the angle enclosed by the center lines of the outlet channel 85 and the inlet channel 84 has a value of approximately 60°, that is, the change of direction amounts to roughly 120°. The inlet channel is initially envisaged as having a diameter of approximately 1 cm, the outlet channel as having a diameter of 0.8 cm and the inlet channel as having a length of about 5 cm. The preferred embodiment shown is preferably realized in plastic.

Figure 9:
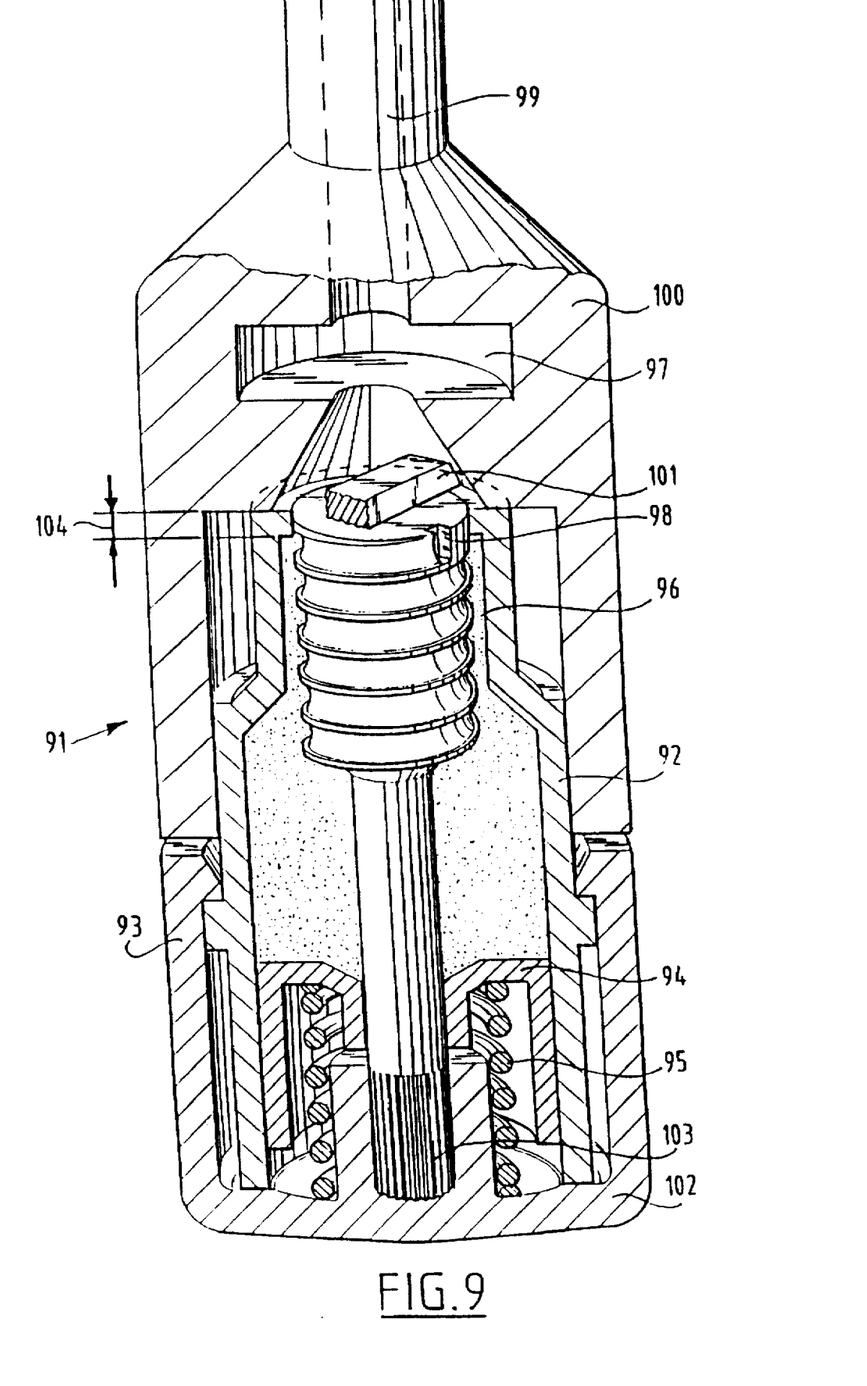
FIG. 9 shows a partially broken away view of a fourth preferred embodiment of the inhaler device according to the present invention.

A fourth embodiment of inhaler device 91 is shown in FIG. 9. The inhaler device 91 includes a housing 92 in which a reservoir 93 of inhalable material, which may be medicinal, is held in a compressed state. Compression within the reservoir 93 is maintained by a movable base 94 biased by spring 95. A transporting screw or worm 96 is provided within the reservoir 93 for transporting the medium out of the reservoir 93 into a whirl chamber 97 through an opening 98. The whirl chamber 97 is coupled to an inhaling conduit 99 which operates substantially the same as the opening 17 or inhaling piece 61 described above. The inhaling conduit 99 and the whirl chamber 97 are formed in an inhaling piece 100 which is placed on the housing 92. The connection between the inhaling piece 100 and the housing 92 may be a snap-on connection or the like so that after the reservoir 93 has been emptied, the inhaling piece 100 can be placed over a new reservoir 93.

A closing piece 101 is positioned to selectively seal off the opening 98 when the opening 98 is aligned with the closing piece 101. The screw or worm 96 is adapted to be rotated by a turning knob 102 connected to the screw or worm 96 through a spline connection 103.

In operation, knob 102 is turned to cause the transporting screw or worm 96 to rotate 180°. The screw or worm 96 is now positioned to an opposed sealed position wherein the closing piece 101 is aligned with the opening 98 to seal off the opening 98. This operation will effectively dispense one dosage of the medium of about 7 to 8 mg. into the whirl chamber 97.

In the inhaler device 91, the thickness, shown at 104, of the threshold of the housing 92 positioned between the reservoir 93 and the whirl chamber 97 is less than the pitch of the thread of the transporting screw or worm 96. Preferably, the thickness 104 of the threshold is less than 3 mm and preferably about 1 mm. This construction minimizes the difficulties in rotating the transporting screw or worm 96 due to the medium within the reservoir 93.

The present invention is not limited to the preferred embodiments shown and described. The rights are determined by the claims following hereinafter.

We claim:

1. A device for inhaling an aerosol, comprising:

a) a housing which has therein a reservoir of an inhalable medium;

b) an inhaling piece placed on said housing;

c) means for holding the inhalable medium in said reservoir in a compressed state comprising a piston and a spring incorporated in said housing; and d) means for transporting the inhalable medium from said reservoir to said inhaling piece in a dose required for the aerosol, said transporting means including a plunger provided with a recess within said plunger and said plunger movable reciprocally counter to the pressure of a plunger spring axially along said plunger between a first position wherein said recess is within said reservoir and a second position wherein said recess is positioned outside of said reservoir and is in communication with said inhaling piece.

2. The inhaler device as claimed in claim 1 wherein the inhalable medium in the reservoir is a powder.

3. The inhaler device as claimed in claim 1, wherein said plunger includes a protrusion received in a groove for causing said plunger to rotate relative to said housing.

4. The inhaler device as claimed in claim 1 wherein said inhaling piece is for sucking indrawn air, along with a dose of the inhalable medium, and said inhaling niece has a whirl chamber incorporated therein, said whirl chamber having a first air intake opening extending to the exterior of said inhaling piece for drawing in a first stream of air from the exterior of said inhaling piece which moves the dose of the inhaler medium, and a second air intake opening extending to the exterior of said inhaling piece spaced from said first air intake opening for drawing in a second stream of air from the exterior of said inhaling piece which collides with the first stream of air, wherein the air drawn in through said first air intake opening moves the dose of the inhalable medium and subsequently collides with the air drawn in along said second air intake opening, and wherein by the collision of two air streams, a whirling is excited within said whirling chamber such that the active constituents of the inhalable medium are released to a sufficient extent with sufficiently a small diameter, wherein the inhalable medium is taken up in said inhaling piece with the two streams of indrawn air with only a small suction force.

5. The inhaler device as claimed in claim 4, wherein a mouth of said inhaling piece is disposed eccentrically of a center line extending through said inhaler device.

6. The inhaler device as claimed in claim 4 further including a guide means for guiding at least one of the air streams and arranged in the vicinity of the center of said inhaling piece.

7. The inhaler device as claimed in claim 6, wherein said guide means is provided with a rounded portion and with a sharp-edged portion.

8. The inhaler device as claimed in claim 6, herein said guide means is provided with a guide portion for guiding at least one of the air streams upward to a mouth of said inhaling piece.

9. The inhaler device as claimed in claim 6, wherein said guide means guide the first air stream at a position upstream of where the first air stream collides with the second air stream.

10. The inhaler device as claimed in claim 4, wherein said first air stream is in a direction generally perpendicular to the second air stream at the position where said air streams collide.

11. The inhaler device as claimed in claim 4 further including at least two mutually interchangeable reservoirs storing different inhalable media.

* * * * *